United States Patent [19]
Abul-Hajj et al.

[11] Patent Number: 5,866,558
[45] Date of Patent: Feb. 2, 1999

[54] 6-ALKYNYL STEROIDS

[75] Inventors: Yusuf J. Abul-Hajj, Minneapolis; Abraham Akanni, St. Paul, both of Minn.

[73] Assignee: Regents of the University of Minnesota, Minneapolis, Minn.

[21] Appl. No.: 852,931

[22] Filed: May 8, 1997

[51] Int. Cl.⁶ .......................... A61K 31/565; C07J 1/00
[52] U.S. Cl. .................. 514/177; 514/178; 552/639; 552/640; 552/647
[58] Field of Search ..................... 552/639, 640, 552/647; 514/177, 178

[56] References Cited

U.S. PATENT DOCUMENTS

| | | | |
|---|---|---|---|
| 4,322,416 | 3/1982 | Metcalf et al. | 424/242 |
| 4,938,949 | 7/1990 | Borch et al. | 424/10 |
| 5,252,565 | 10/1993 | Peet et al. | 514/177 |

FOREIGN PATENT DOCUMENTS

| | | | |
|---|---|---|---|
| 63-145297 | 6/1963 | Japan | C07K 3/20 |
| 63045294 | 2/1988 | Japan . | |

OTHER PUBLICATIONS

Akkani, A., et al., "6B–Propynyl–Substituted Steroids: Mechanism–Based Enzyme–Activated Irreversible Inhibitors of Aromatase", *J. Med. Chem.*, 40, 3263–3270, (1997).

Campbell, J.A., et al., "6–Methyl Steroids in the Androstane Series", *J. Am. Chem.*, LXXX, 4717–4721, (1958).

Kitz, R., et al., "Esters of Methanesulfonic Acid as Irreversible Inhibitors of Acetylcholinesterase", *J. of Biol. Chem.*, 237, No. 10, 3245–323249, (1962).

Ryan, K.J., "Biological Aromatization of Steroids", *J. of Biol. Chem.*, 234, No. 2, 268–272, (1959).

63–045294 Feb. 26, 1988 Japan C07J 1/00 Partial translation of pp. 1237–1238, 1247–1248 and 1253–1254 (6 pages).

*Primary Examiner*—Allen J. Robinson
*Assistant Examiner*—Barbara Badio
*Attorney, Agent, or Firm*—Schwegman, Lundberg, Woessner & Kluth, P.A.

[57] ABSTRACT

Compounds of formula I:

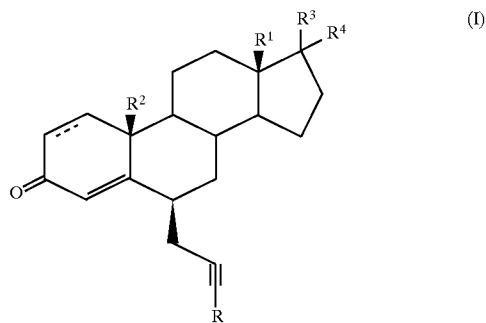

wherein R, $R^1$, $R^2$, $R^3$, and $R^4$ have any of the values defined in the specification, and their pharmaceutically acceptable salts, are inhibitors of aromatase, and are useful for treating diseases such as breast cancer, in mammals. Also disclosed are pharmaceutical compositions, processes for preparing compounds of formula (I) and intermediates useful for preparing compounds of formula I.

21 Claims, 2 Drawing Sheets

(III, R¹ = R² = methyl)

6-ALKYNYL STEROIDS

This invention was made with government support under grant TW-05132 from the National Institutes of Health. The government has certain rights in this invention.

BACKGROUND OF THE INVENTION

The female sex hormones estradiol and estrone are involved in many physiological processes and have been studied extensively. The formation of these steroids is regulated by a number of enzymes. The enzyme aromatase is the rate limiting enzyme in the conversion of testosterone and androstenedione to estradiol and estrone. As disclosed in U.S. Pat. No. 4,322,416, granted 30 Mar. 1982, certain 10-alkynyl steroids that can regulate or inhibit aromatase may have the potential to treat clinical conditions which are potentiated by the presence of estrogens. Aromatase inhibitors have been used for the treatment of conditions such as gynecomastia, male infertility associated with oligospermia, fertility control, endometrial cancer associated with production of high levels of estrogens, and most importantly, for treatment of breast cancer.

Breast cancer is one of the leading causes of death in women in the United States. About two-thirds of breast cancers are hormone independent and are treated with radiation or chemotherapy. The remaining one-third are hormone-dependent and are treated with either endocrine ablative therapy, or with the antiestrogen tamoxifen, or with aromatase inhibitors.

Aromatase inhibitors have also been shown to be effective as second line therapeutic agents in tamoxifen resistant breast cancer. In March 1996, the FDA approved the first Type II aromatase inhibitor for use in the United States. Other nonsteroidal aromatase inhibitors are currently being evaluated for safety and efficacy. The steroidal aromatase inhibitor, 4-hydroxyandrostenedione, has been approved in the United Kingdom for treatment of breast cancer. Aromatase inhibitors are currently recognized as useful tools for the management and remission of metastatic breast cancer. Therefore, there is a need for effective aromatase inhibitors to treat breast cancer and other cancers.

SUMMARY OF THE INVENTION

The present invention relates to 6-alkynyl steroids which are aromatase inhibitors. According to the invention there is provided a compound of the invention which is a compound of formula I:

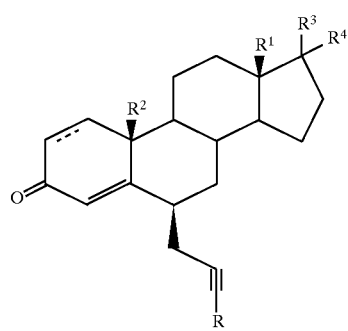

wherein
the bond represented by - - - is present or absent;
R is hydrogen or $(C_1–C_4)$ alkyl;
$R^1$ is methyl or ethyl;
$R^2$ is hydrogen or methyl;
$R^3$ is hydrogen and $R^4$ is $OR^5$; or $R^3$ and $R^4$ taken together are oxo(=O); and
$R^5$ is H or $(C_2–C_4)$ alkanoyl.

Pharmaceutical compositions comprising a compound of formula (I), in combination with a pharmaceutically acceptable carrier are also within the scope of the invention, as is the use of unit dosage forms comprising an effective aromatase inhibitory amount of said composition to treat estrogen mediated conditions such as cancer, e.g., breast cancer, in a mammal afflicted with such a condition.

DETAILED DESCRIPTION OF THE INVENTION

Figure 1:
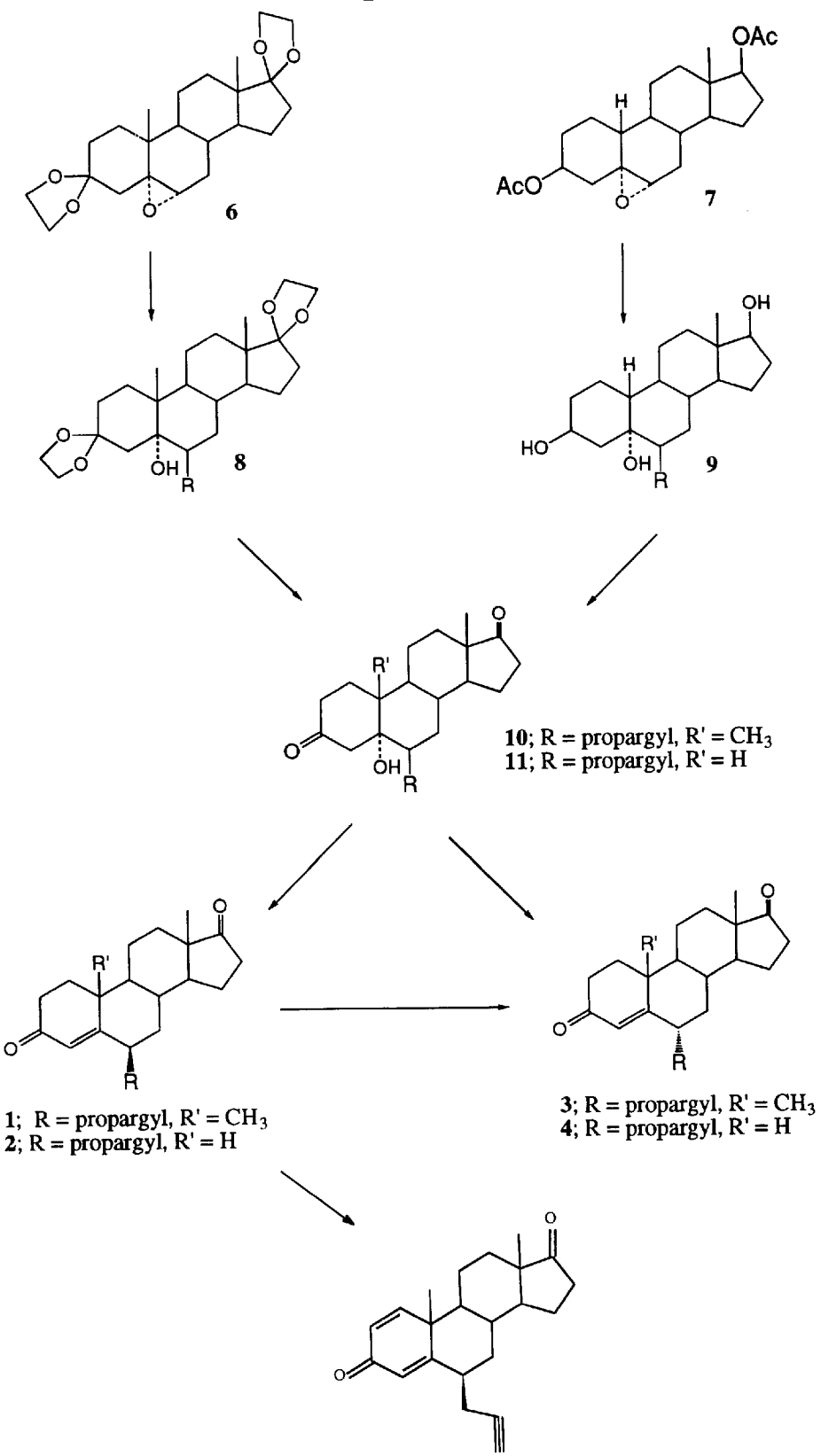
FIG. 1 shows a synthetic scheme for preparing compounds of formula I.
Figure 2:
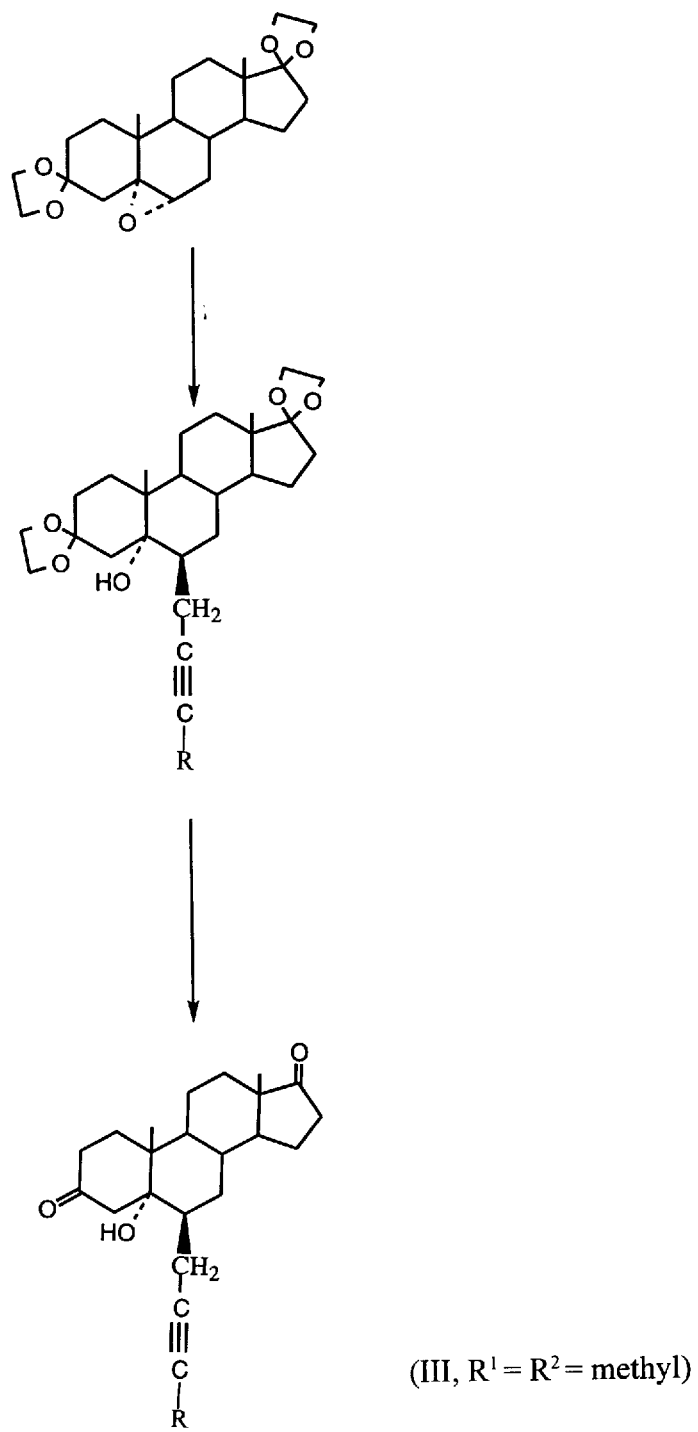
FIG. 2 shows a synthetic scheme for preparing compounds of formula III.

The following definitions are used, unless otherwise described. Alkyl, alkanoyl, etc. denote both straight and branched groups; but reference to an individual radical such as "propyl" embraces only the straight chain radical, a branched chain isomer such as "isopropyl" being specifically referred to.

The compounds of the invention are optically active. Preferably, the B/C and C/D ring junctions are trans, and $R^1$ and $R^2$ are in the β-orientation, as in the natural androstane and estrane series, wherein a wedged bond indicates a bond extending above the plane of the ring system. The alkynyl group at carbon 6 is also in the β-orientation. While compounds having the natural steroidal configuration as described are the active inhibitors, mixtures of the compounds with their optical antipodes are also included within the scope of the invention. It may be preferred to use a compound of the invention in a form which is characterized as containing, for example, at least 80%, 95%, 98%, or 99% enantiomeric excess.

Some compounds of the invention may exhibit polymorphism. It is to be understood that the present invention encompasses any polymorphic form of a compound of the invention, it being well known in the art how to determine aromatase activity of a given form using the test described herein, or similar tests which are well known in the art.

Specific values listed below for radicals, substituents, and ranges, are for illustration only, and they do not exclude other defined values or other values within defined ranges for the radicals and substituents.

Specifically, $(C_1–C_4)$alkyl can be methyl, ethyl, propyl, or butyl; and $(C_2–C_4)$ alkanoyl can be acetyl, propanoyl or butanoyl.

A specific value for R is hydrogen, for $R^1$ is methyl; for $R^2$ is hydrogen or methyl; for $R^4$ is hydroxy or acyloxy; and for $R^5$ is hydrogen or propionyl. A specific group of compounds are compounds of formula I wherein $R^3$ is hydrogen and $R^4$ is OH; or $R^3$ and $R^4$ taken together are oxo.

Specific compounds of the invention include but are not limited to the following: 6β-(2-propynyl)androst-4-ene-3,17-dione; 6β-(2-propynyl)estr-4-ene-3,17-dione; 6β-(2-propynyl)androsta-1,4-diene-3,17-dione; 6β-(2-butynyl)-androst-4-ene-3,17-dione; and 17β-acetoxy-6β-(2-propynyl)androst-4-ene-3-one.

A preferred group of compounds of the invention are compounds wherein the bond represented by - - - is absent. Another preferred group of compounds of the invention are compounds wherein $R^3$ and $R^4$ taken together are oxo.

A preferred embodiment of the invention is the compound of formula II.

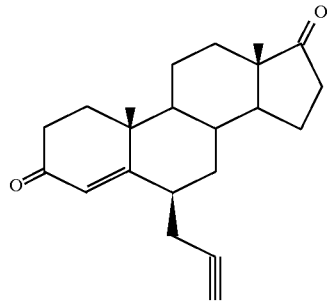

Processes for preparing compounds of formula I are provided as further embodiments of the invention and are illustrated by the following procedures in which the meanings of the generic radicals are as given above unless otherwise qualified.

Compounds of formula I wherein the bond represented by - - - is absent can be prepared from a corresponding alcohol of formula III by dehydration.

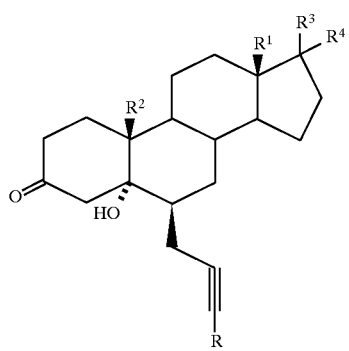

The dehydration may be carried out under conditions which are standard in the art, or may conveniently be carried out under conditions similar to those described in Example 1.

Compounds of formula I wherein the bond represented by - - - is present can be prepared from a corresponding compound of formula I wherein the bond represented by - - - absent by oxidation. The oxidation may be carried out under conditions which are standard in the art, or may conveniently be carried out under conditions similar to those described in Example 3.

An intermediate alcohol of formula III ($R^2$, $R^2$=methyl) can be prepared as shown schematically in FIG. 1. Reaction of the bis(ethylene acetal) of 5α,6α-epoxy androstanedione with an organo-metallic reagent, for example, a Grignard reagent of formula R-C: C—$CH_2$MgBr, affords the corresponding 5α-hydroxy-6β alkynl analog. Deprotection, for example under conditions similar to those described in Example 1, sub-part 2, gives the desired alcohol of formula III ($R^1$, $R^2$=methyl). The starting material 3,3:17,17-bis (ethylenedioxy)androstane-5α,6α-epoxide was prepared using a procedure similar to that described in Campbell, J. A., Babcok, J. C. & Hogg, J. A., J. Am. Chem. Soc., 80, 4717 (1980).

In addition to intermediates of formula III, intermediates of the general formula IV or V are useful for preparing compounds of the invention.

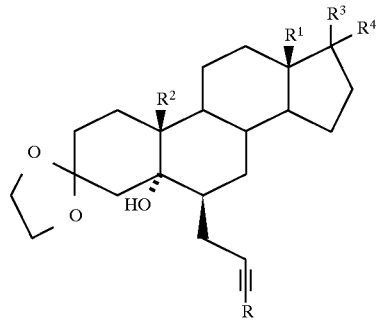

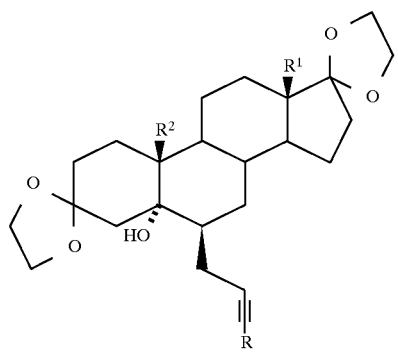

Accordingly, novel intermediates of the formula III, IV or V wherein $R^1$ to $R^5$ have any of the values, particular values or preferred values defined herein, are included as further features of the invention.

Japanese Patent application 63/45294 hereinafter '294) purports to disclose the synthesis of 6β-propargyl androstenedione. It has been determined, however, that the synthetic steps disclosed in '294 yield the 6α-isomer and not the 6β-isomer as reported. Using the procedure described in Example 1 herein, the 6β-isomer has been prepared. This compound has been characterized, and its structure has been confirmed by X-ray crystallography. A comparison of the physical data: 1) for the 6β-isomer, 2) for the α-isomer, and 3) for the compound discloses in '294 as compound I-10 at page 1248 therein follows.

| 6β-propargyl-4-androstenedione | 6α-propargyl-androstenedione |
|---|---|
| m.p. = 159–160° C. | m.p. = 110–112° C. |
| IR (KBR): 3245, 2120, 1734, 1662 $cm^{-1}$ | IR (KBR): 3245, 2150, 1740, 1675 $cm^{-1}$ |
| $^1$H-NMR: δ 0.93 (s, 3H, 18-H) | $^1$H-NMR: δ 0.93 (s, 3H, 18-H) |
| 1.26 (s, 3H, 19-H) | 122 (s, 3H, 19-R) |
| 2.6–2.8 (m, 1H, propargyl) | 23–25 (m, 1H, propargyl) |
| 5.84 (s, 1H, 4-H) | 5.81 (s, 1H, 4-H) |

Physical Data reported in '294 for compound I-10 m.p.=116°–118° C.

IR(KBR): 3300, 1733, 1665, 1660 $cm^{-1}$ $^1$H-NMR: δ0.93 (s, 3H, 18-H)

1.22 (s, 3H, 19-H)

2.3–2.5 (m, 1H, J=2.5 Hz, propargyl)

5.81 (s,1H, 4-H)

From this comparison, it is clear that the compound which results from the synthetic procedure disclosed in '294 is the 6α-isomer, and not the 6β-isomer. It has been discovered that treatment of (1) with p-toluenesulfonic acid for an extended period of time (16 hours), as described in '294, yields the 6α-compound (2).

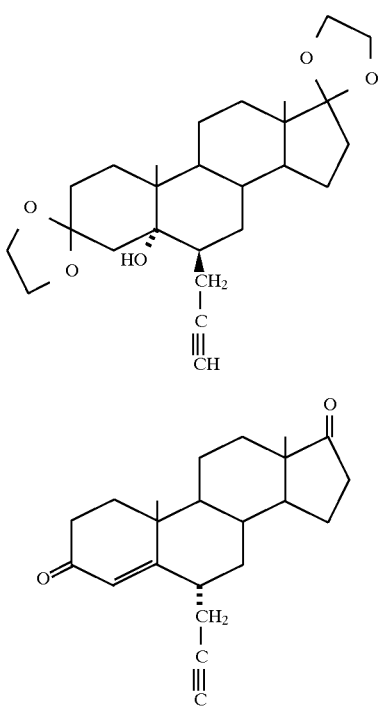

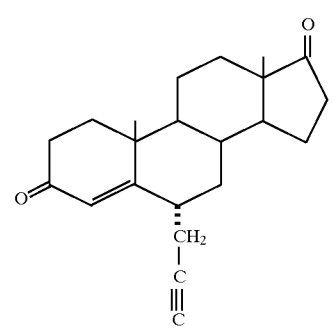

Japanese Patent application 63/45294 does not teach the 6β-compound or how to prepare it. Therefore, the 6β-propargyl androstenedione disclosed herein as well as the processes and intermediates useful for preparing the 6β-propargyl androstenedione are novel.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable salts of inorganic acids may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of the invention can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0. 1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949. Dosages may be extrapolated to some extent from those found to be effective for other steroidal aromatase inhibitors.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%. Single dosages for injection, infusion or ingestion will generally vary between 10–1500 mg, and may be administered, i.e., 1–3 times daily, to yield levels of about 0.5–50 mg/kg, for adults. For example, doses of 10–600 mg for oral administration, 10–200 mg for intramuscular injection, and 10–100 mg for intravenous injection may preferably be administered.

Accordingly, the invention includes a pharmaceutical composition comprising a compound of formula I as described hereinabove; and a pharmaceutically acceptable diluent or carrier.

The aromatase inhibitory properties of compounds of the invention can be demonstrated using standard pharmacological models, including those described below as Tests A, B, and C.

Test A. Enzyme Affinity Assay

Microsomes were obtained from human placentas after normal deliveries and prepared as described previously (Ryan, K. J. "Biological aromatization of steroids" J Biol. Chem. 1959, 234, 266–272). Following isolation of the microsomal pellets (washed twice), they were lyophilized and stored at −20° C. These preparations can be kept for 6 months without loss of activity.

The enzyme affinity of the present inhibitors is determined by measuring their competitive inhibition of the conversion of $^3$H-androstenedione to estrogens, using a method similar to that described in U.S. Pat. No. 4,322,416 at column 12, lines 24–68. The enzymatic activity is related to the % tritium released from $^3$H-androstenedione which appears as $^3$H$_2$O. The activity of each concentration of inhibitor is calculated as a % of the vehicle control, which is arbitrarily set at 100%. The molar concentration of each inhibitor which reduces enzyme activity by 50% is called the 50% Inhibition Concentration, IC$_{50}$. These values for 6β-(2-propynyl)-androst-4-ene-3,17-dione and the reference compounds 6α-(2-propynyl)androst-4-ene-3,17-dione, aminoglutethimide, 4-hydroxyandrostenedione, 10-(2-propynyl)estr-4-ene-3,17-dione, and androst-1,4,6-triene-3,17-dione are shown in Table 1. The 6α-propynyl compound has greater enzyme affinty than other known inhibitors, which have been used as antifertility agents in rodents or to block peripheral aromatization in patients with breast cancer. The apparent Ki values for these compounds are shown in Table 1.

TABLE 1

| Inhibitor | IC$_{50}$# | Ki* | Type of Inhibition |
|---|---|---|---|
| 6β-Propargyl AD | 0.022 | 9.8 | Irreversible/Inactivation |
| 6β-Propargyl AD | 0.46 | 87.5 | Reversible |
| 6β-Propargyl ED | 0.098 | 43.5 | Irreversible/Inactivation |
| 6α-Propargyl ED | 0.43 | — | Reversible |
| 10β-Propargyl ED | 0.042 | 26.7 | Irreversible/Inactivation |
| 4-Hydroxy AD | 0.25 | 40.8 | Irreversible/Inactivation |
| 1,4,6-ATD | 0.89 | 136.5 | Irreversible/Inactivation |
| Aminoglutethimide | 3.2 | — | Reversible |

Abbreviations:
AD = 4-androstene-3,17-dione;
ED = 4-estrenedione-3,17-dione;
ATD = androstatriene-3,17-dione;
(uM);
* (uM).

6α-Propargyl AD and 6α-propargyl ED were prepared by treating the corresponding 6β isomers with a 2.5% (v/v) HCl/CHCl$_3$ solution at room temperature for two hours.

Test B. Evaluation of Time-Dependent Inhibition

Compounds of the invention having IC$_{32}$=10$^{-7}$M, were evaluated for time-dependent inhibition, using a method similar to that described in U.S. Pat. No. 4,322,416 at column 13, lines 29–62.

Test C. K$_i$ Determination

Compounds which showed a time-dependent inhibition in Test B were then assayed to establish the inhibition constant, K$_i$, which is the apparent dissociation constant for the enzyme-inhibitor complex. This determination requires measurements at initial velocities of enzyme reaction. The enzyme activity is determined following different preincubation times at various inhibitor concentrations when assayed at a substrate concentration of at least ten times the Km of androstenedione. The apparent Ki$_{(inact)}$ values for representative compounds of the invention are shown in Table 2. These data indicate that the 6β-propargyl androstenedione is irreversibly bound to the enzyme with an affinity for the enzyme site which is about five times greater than that for the natural substrate androstenedione, which has an affinity (Km) of $5.5 \times 10^{-8M}$.

TABLE 2

Enzyme Kinetic Parameters for 6β-Propargyl-17-Ketosteroids#

| Compound | T$_{1/2}$ (min) | k$_{cat}$ (sec$^{-1}$) | App. Ki$_{(inact)}$ (nM)(×10$^{-6}$) |
|---|---|---|---|
| 6β-Propargyl AD | 7.7 | 1.5 × 10$^{-3}$ | 46.8 |
| 6β-Propargyl ED | 9.75 | 1.2 × 10$^{-3}$ | 15.4 |

Kinetic parameters, and T$_{1/2}$of enzyme inhibition were determined by the methods of Kitz and Wilson, "Esters of methansulfonic acid as reversible inhibitors of acetylcholinesterase" J. Biol. Chem. 1962, 237, 3245–1079.

In general, compounds of the invention which were tested demonstrated the ability to inhibit aromatase in the above described tests A, B, and C, The compound 6β-propynyl 4-androstenedione demonstrated inhibitory properties which are superior to other known aromatase inhibitors. Results from test C, in particular, demonstrate that the 6β compounds of the invention are mechanism-based irreversible aromatase inhibitors, which result in enzyme inactivation. In contrast, the 6α-alkynyl analogs of androstenedione are competitive inhibitors, which do not show irreversible inhibition of aromatase. Additionally, the 6β compounds are substantially more potent aromatase inhibitors than the corresponding 6α compounds.

Compounds of the invention are inhibitors of aromatase. As such, they may be useful in treating disorders potentiated by the presence of estrogens. Such disorders include: hyperestrogenemia; gynecomastia, male infertility from elevated estrogen levels; endometrial cancer; and hyperestrogenemia, which may precede myocardial infarction. The compounds may also have value in the treatment of breast cancer and other estrogen-induced or stimulated tumors, or as anti-infertility agents to prevent ovulation or implantation. Accordingly, the invention includes a method for treating a disease in a human or other mammal in need thereof in which aromatase has been implicated and inhibition of its action is desired, comprising administering to said human or mammal an effective amount of a compound of formula I or a pharmaceutically acceptable salt thereof. The invention also includes a method for inhibiting aromatase in a mammal comprising administering to said mammal an effective amount of a compound of formula I; or a pharmaceutically acceptable salt thereof. Additionally, compounds of the invention can be used in vitro or in vivo as pharmacological and biochemical tools to assist in the discovery and evaluation of other aromatase inhibitors.

Additionally, alcohols of the general formula III:

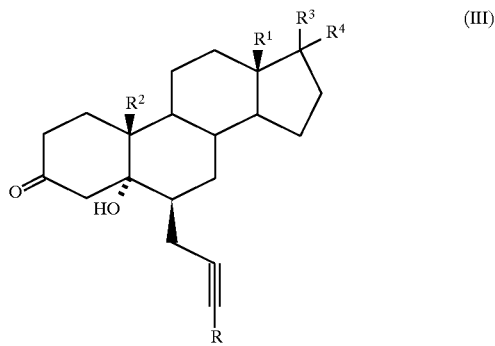

have been found to function as prodrugs for compounds of formula I. For example, compound (3) was incubated with rat liver homogenates, and found to dehydrate in the presence of the homogenates to give compound (4).

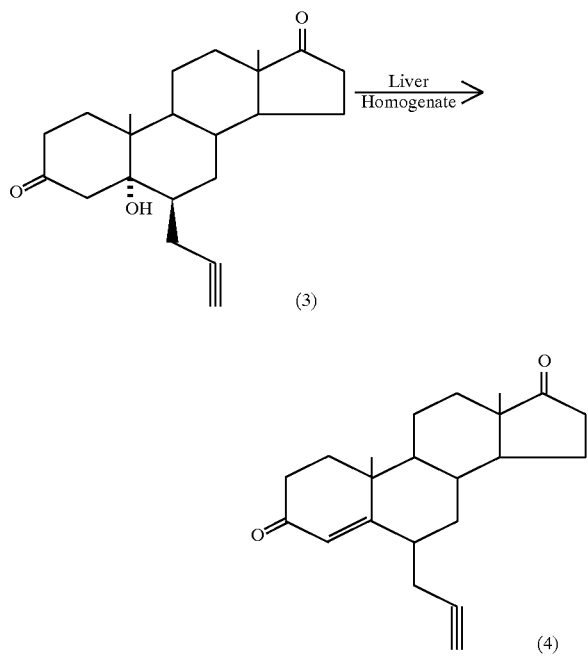

Thus, alcohols of the general formula III are capable of functioning as prodrugs for compounds of the invention.

Accordingly, the invention includes a compound of formula III, wherein R to $R^5$ are defined as above; or a pharmaceutically acceptable salt thereof. The invention also includes a pharmaceutical composition comprising a compound of formula III; or a pharmaceutically acceptable salt thereof; and a pharmaceutically acceptable diluent or carrier. Because alcohols of formula III are capable of acting as prodrugs for compounds of formula I, it may be advantageous to use an alcohol of formula III in place of a corresponding compound of formula I in any of the methods disclosed herein. Accordingly, the invention includes a method for treating a disease in a human or other mammal in need thereof in which aromatase has been implicated and inhibition of its action is desired, comprising administering to said human or mammal an effective amount of a compound of formula III; or a pharmaceutically acceptable salt thereof. The invention also includes a method for inhibiting aromatase in a mammal comprising administering to said mammal an effective amount of a compound of formula III; or a pharmaceutically acceptable salt thereof.

The invention will now be illustrated by the following non-limiting examples in which unless otherwise stated: melting points were determined on a Fisher Jones melting point apparatus and are uncorrected; infrared spectra were obtained on a Nicolet 5DXC FT-IR spectrometer; nuclear magnetic resonance (NMR) spectra were obtained with a GE 300 MHz spectrometer using TMS as internal standard; mass spectral data were obtained on a VG 7070 E-HF, and a Finnegan MAT 95; thin layer chromatography (TLC) was performed on a precoated silica gel plate (Silica Gel GF; Analtech, Inc., Newark, N.J.); silica gel (200–400 mesh, Aldrich Chemical Company, Milwaukee, Wis.) was used for all column chromatography; ultracentrifugation was performed on a Beckman L2165B ultracentrifuge; radioactivity was determined on a Beckman LS-100 liquid scintillation counter; organic solutions were dried over anhydrous sodium sulfate; androstenedione was purchased from Steraloids (Wilton, N.H.); [1β-$^3$H]androstenedione (24 Ci/mmol) was purchased from New England Nuclear (Boston, Mass.); and all other chemicals were reagent grade and were obtained from Aldrich Chemical Company or Sigma Chemical Company (St. Louis, Mo.).

EXAMPLES

EXAMPLE 1. 6β-Propargyl-4-androstene-3,17-dione (1).

6β-Propargyl-5α-hydroxyandrostane-3,17-dione (10) (0.3 mmol) was dissolved in dry pyridine (10 ml), cooled in an ice-bath and thionyl chloride was added. After stirring for 3–5 minutes, the reaction mixture was poured over ice-water, extracted with ethyl acetate, washed (water), dried, and evaporated in vacuo. The residue was subjected to column chromatography (hexane/ethyl acetate). Recrystallization from acetone/hexane gave the title compound (60% of the analytical product); m.p. 159°–160° C.; IR (KBr) 3245, 2120, 1734, and 1662 (C=O) cm$^{-1}$; $^1$H-NMR (CDCl$_3$) δ 0.93 (s, 3H, 18-CH$_3$), 1.26 (s, 3H, 19-CH$_3$), 2.6–2.8 (m, 1H), 5.84 (s, 1H, 4-H).

The intermediate 6β-propargyl-5α-hydroxyandrostane-3,17-dione (10) was prepared as follows.

(a) 3,3:17,17-bis(Ethylenedioxy)androstane-5α,6α-epoxide (6). To a solution of 3,3:17,17-bis(ethylenedioxy)androst-5-ene (3 g, 8 mmol) in dichloromethane (50 ml) was added m-chloroperbenzoic acid (1.95 g, 11.3 mmol). The resulting mixture was stirred at room temperature for 3 hours, diluted with dichloromethane (100 ml), washed (10% Na$_2$S$_2$O$_3$, 5% NaHCO$_3$, brine, and water) and dried. The solvent was evaporated in vacuo, and the residue separated using column chromatography by eluting with hexane/ethyl acetate to afford the 5α,6α-epoxide (1.3 g, 40% yield) and the 5β,6β-epoxide (700 mg, 23%). Crystallization from acetone/hexane afforded the 5α,6α-epoxide; m.p. 222°–223°; $^1$H-NMR (CDCl$_3$) δ 0.79 (s, 3H, 18-CH$_3$) 1.07 (s, 3H, 19-CH$_3$), 2.36 (d, 1H, 4-H), 2.81 (d, 1H, 6β-H), 3.8–4.08 (m, OCH$_2$CH$_2$O×2).

(b) 6β-Propargyl-3,3:17,17-bis(ethylenedioxy)androstane-5α-ol (8). Grignard reagent was prepared from Mg (0.84 g) and propargyl bromide (4.5 ml) in dry ether with mercuric chloride (50 mg) as initiator under an atmosphere of nitrogen. To the cooled Grignard reagent, CuCl (50 mg) was added. After stirring at room temperature for 5–10 minutes, the epoxy diketal 6 (600 mg, 1.5 mmol) in dry THF (50 ml) was added. After 2–3 hours, saturated ammonium chloride solution was added and the product was isolated with ethyl acetate. The ethyl acetate extract was washed (brine water), dried, and removed in vacuo. The residue was subjected to column chromatography on silica gel and eluting with 25% ethyl acetate in hexane to give the product 8 in 70% yield; m.p. 160°–162°; IR (KBr) 3270, 3294, and 2100 cm$^{-1}$; $^1$H-NMR (CDCl$_3$) δ 0.85 (s, 3H, 18-CH$_3$), 0.94 (s, 3H, 19-CH$_3$), 3.8–4.0 (m, OCH$_2$CH$_2$O×2).

(c) 6β-Propargyl-5α-hydroxyandrostane-3,17-dione (10). The 6β-propargyl bisketal 8 (0.6 mmol) was dissolved in acetone (30 ml) and p-TSOH (5 mg) was added. The reaction mixture was stirred at room temperature for 3 hours, diluted with ethyl acetate, washed (5% NaHCO$_3$, brine, water) and dried. The ethyl acetate was removed in vacuo and the product was purified by column chromatography to yield the dione 90% yield; m.p. 145°–146° C.; IR (KBr) 3475 (C C—H), 3300 (OH), 2100, 1735 and 1715 (C═O) cm$^{-1}$; $^1$H-NMR (CDCl$_3$) δ 0.91 (s, 3H, 18-CH$_3$), 1.21 (s, 3H 19-CH$_3$), 3.0 (d, 1H, 4β-H).

The starting material 3,3:17,17-bis(ethylenedioxy)androstane-5α,6α-epoxide used in sub-part (a) above can be prepared using a procedure similar to that described in Campbell, J. A., Babcok, J. C. & Hogg, J. A., J. Am. Chem. Soc. 80, 4717 (1980).

EXAMPLE 2. 6β-Propargyl-4-estrene-3,17-dione (2).

Using a procedure similar to that described at Example 1 except replacing the 6β-propargyl-5α-hydroxyandrostane-3,17-dione (10) used therein with 6β-propargyl-5α-hydroxyestrane-3,17-dione (11), the title compound was prepared; 60%; m.p. 194°–195° C. (from acetone/hexane); $^1$H-NMR (CDCl$_3$) δ 0.94 (s, 3H, 18-CH$_3$), 2.73 (m, 1H), 5.94 (s, 1H, 4-H).

The intermediate 6β-propargyl-5α-hydroxyestrane-3,17-dione (11) was prepared as follows.

(a) 3β–17β-Diacetoxyestrane-5α,6α-epoxide (7). To a solution of 2 g of the 3β,17β-diacetoxyestr-5-ene in dichloromethane (70 ml) was added 1.4 g metachloroperbenzoic acid. The mixture was stirred at room temperature for about 2 hours, diluted with 50 ml dichloromethane and washed successively with 10% Na$_2$S$_2$O$_3$, 5% NaHCO$_3$ and water. The organic layer was dried, and evaporated in vacuo to yield a mixture of the α- and β-epoxides which were separated using column chromatography. Elution with hexane/ethyl acetate (3:1) gave 60% yield of the 5α,6α-epoxide 7; $^1$H-NMR (CDCl$_3$) δ 0.76 (s, 3H, 18-CH$_3$), 2.02 (s, 3H, 17-OAc), 2.03 (s, 3H, 3-OAc), 2.98 (d, 1H, 6β-H), 4.56 (t, 1H, 17α-H), 4.95 (m, 1H, 3α-H).

(b) 6β-Propargyl-3β,5α,17βestrane-5α-ol (9). Using a procedure similar to that described in Example 1, sub-part (b), except replacing the diketal (6) used therein with the diacetate (7), the propargyl alcohol was prepared; m.p. 214°–216° (from acetone/hexane); $^1$H-NMR (acetone d$_6$) δ 0.74 (s, 3H, 18-CH$_3$), 3.92 (m, 1H, 3α-H), 3.56 (t, 1H, 17α-H).

(c) 6β-Propargyl-5α-hydroxyestrane-3,17-dione (11). The 6β-propargyl triol 9 (0.6 mmol) was dissolved in acetone (30 ml) and cooled to 4° C. followed by dropwise addition of Jone's reagent until the solution turned light brown. The reaction mixture was stirred at 4° C. for approximately 5 minutes, was diluted with water, extracted with ethyl acetate, washed (5% NaHCO$_3$, brine, water) and dried, The ethyl acetate was evaporated in vacuo and the product obtained was purified by column chromatography to yield the dione 11 in 90% yield: m.p. 186°–188° C.; $^1$H-NMR (CDCl$_3$) δ 0.91 (s, 3H, 18-CH$_3$), 2.65 (d, 1H, 6-H).

EXAMPLE 3. 6β-Propargyl-1,4-androstadiene-3,17-dione (12).

To a solution of 6β-propargyl-4-androstene-3,17-dione (1) (160 mg, 0.5 mmol) in dry dioxane (30 mL) was added dichlorodicyanobenzoquinone (DDQ, 150 mg, 0.6 mmol), and the reaction mixture was refluxed with stirring for 6 hours. Dilution with 30 mL dichloromethane followed by washing (1% NaOH, water), drying and evaporation in vacuo, gave 125 mg of crude product. The residue was purified by chromatography over silica gel and the product was recrystallized from acetone/hexane to give 95 mg (60% yield) of the title compound (12).

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

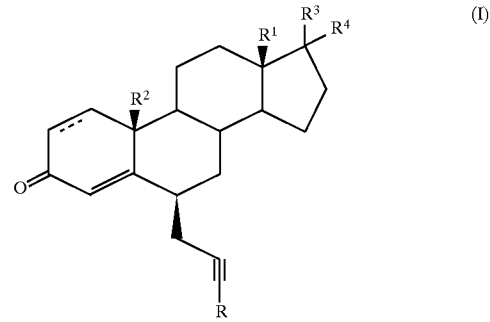

wherein
the bond represented by - - - is present or absent;
R is hydrogen or (C$_1$-C$_4$) alkyl;
R$^1$ is methyl or ethyl;
R$^2$ is hydrogen or methyl;
R$^3$ is hydrogen and R$^4$ is OR$^5$; or R$^3$ and R$^4$ taken together are oxo; and $R^5$ is H or $(C_2-C_4)$ alkanoyl;

or a pharmaceutically acceptable salt thereof.

2. A compound of claim 1, wherein R is hydrogen.

3. A compound of claim 1, wherein $R^1$ is methyl.

4. A compound of claim 1, wherein $R^2$ is hydrogen.

5. A compound of claim 1, wherein $R^2$ is methyl.

6. A compound of claim 1, wherein $R^3$ is hydrogen and $R^4$ is OH; or $R^3$ and $R^4$ taken together are oxo.

7. A compound of claim 6 wherein the bond represented by - - - is absent.

8. A compound of claim 1 which is 6β-(2-propynyl)androst-4-ene-3,17-dione.

9. A compound of claim 1 which is 17β-hydroxy-6β-(2-propynyl)-androst-4-ene-3-one propionate.

10. A compound of claim 1 which is 17β-hydroxy-6β-(2-propynyl)-androst-4-ene-3-one acetate.

11. A compound of claim 1 which is 6β-(2-propynyl)androsta-1,4-diene-3,17-dione.

12. A compound of claim 1 which is 6β-(2-propynyl)estr-4-ene-3,17-dione.

13. A compound of claim 1 which is 17β-hydroxy-6β-(2-propynyl)estr-4-ene-3-one.

14. A compound of claim 1 which is 17β-hydroxy-6β-(2-propynyl)est-4-ene-3-one acetate.

15. A compound of claim 1 which is 6β-(2-propynyl) androst-4-ene-3,17-dione; 6β-(2-propynyl)estr-4-ene-3,17-dione; 6β-(2-propynyl)adrosta-1,4-diene-3,17-dione; 6β-(2-butynyl)androst-4-ene-3,17-dione; or 17β-acetoxy-6β-(2-propynyl)androst-4-ene-3-one.

16. A method for treating a diseasein a human or other mammal in need thereof in which aromatase has been implicated and inhibition of its action is desired, comprising administering to said human or mammal an effective amount of a compound of formula I; or a pharmaceutically acceptable salt thereof.

17. A method as described in claim 16 wherein the disease is hyperestrogenemia.

18. A method as described in claim 16 wherein the disease is breast cancer.

19. A method as described in claim 16 wherein the disease is infertility.

20. A method for inhibiting aromatase in a mammal comprising administering to said mammal an effective amount of a compound of formula I; or a pharmaceutically acceptable salt thereof.

21. A pharmaceutical composition comprising a compound of claim 1, in combination with a pharmaceutically acceptable diluent or carrier.

* * * * *

UNITED STATES PATENT AND TRADEMARK OFFICE
CERTIFICATE OF CORRECTION

PATENT NO.: 5,866,558
DATED: 2/2/99
INVENTOR(S): Abul-Hajj et al.

It is certified that errors appear in the above-identified patent and that said Patent is hereby corrected as shown below:

In column 4, line 32 delete "hereinafter" and insert --(hereinafter--, therefore.
In column 8, line 25 delete "$K_j$" and insert --$K_i$--, therefore.
In column 14, line 4 delete "diseasein" and insert --disease in--, therefore.

Signed and Sealed this

Ninth Day of May, 2000

*Attest:*

Q. TODD DICKINSON

*Attesting Officer*     *Director of Patents and Trademarks*